United States Patent [19]

Bartlett

[11] Patent Number: 4,638,806
[45] Date of Patent: Jan. 27, 1987

[54] RECTAL HEMORRHOID THERAPEUTIC APPARATUS

[75] Inventor: Lawrence D. Bartlett, Hartford, Ky.

[73] Assignee: Robert T. Johnson, Hartford, Ky. ; a part interest

[21] Appl. No.: 753,193

[22] Filed: Jul. 9, 1985

[51] Int. Cl.⁴ .............................................. A61F 7/12
[52] U.S. Cl. ..................................... 128/400; 128/401
[58] Field of Search ................. 128/400, 401; 604/113

[56] References Cited

U.S. PATENT DOCUMENTS

| | | | |
|---|---|---|---|
| 1,011,606 | 12/1911 | Fulton | 128/400 X |
| 1,234,106 | 7/1917 | Hodgson | 128/401 X |
| 1,287,549 | 12/1918 | Wilson | 128/401 X |
| 2,026,747 | 1/1936 | Nemzek | 128/400 X |
| 2,536,001 | 12/1950 | Chase | 604/113 X |

*Primary Examiner*—Anton O. Oechsle
*Attorney, Agent, or Firm*—Edwin E. Greigg

[57] ABSTRACT

The invention comprehends a novel, adjustable, flexible inserter head having a double lumen fluid feed via a hand pump from a reservoir means. The invention includes spring means to protect the outlet of fluid from collapse of the head cover by disposition over an internal outlet rod through which the cryogenic fluid exits to the reservoir. The stationary rod can be replaced so as to shorten the inserter and vary the original extended, slim head cover to a blunter, stouter configuration.

3 Claims, 2 Drawing Figures

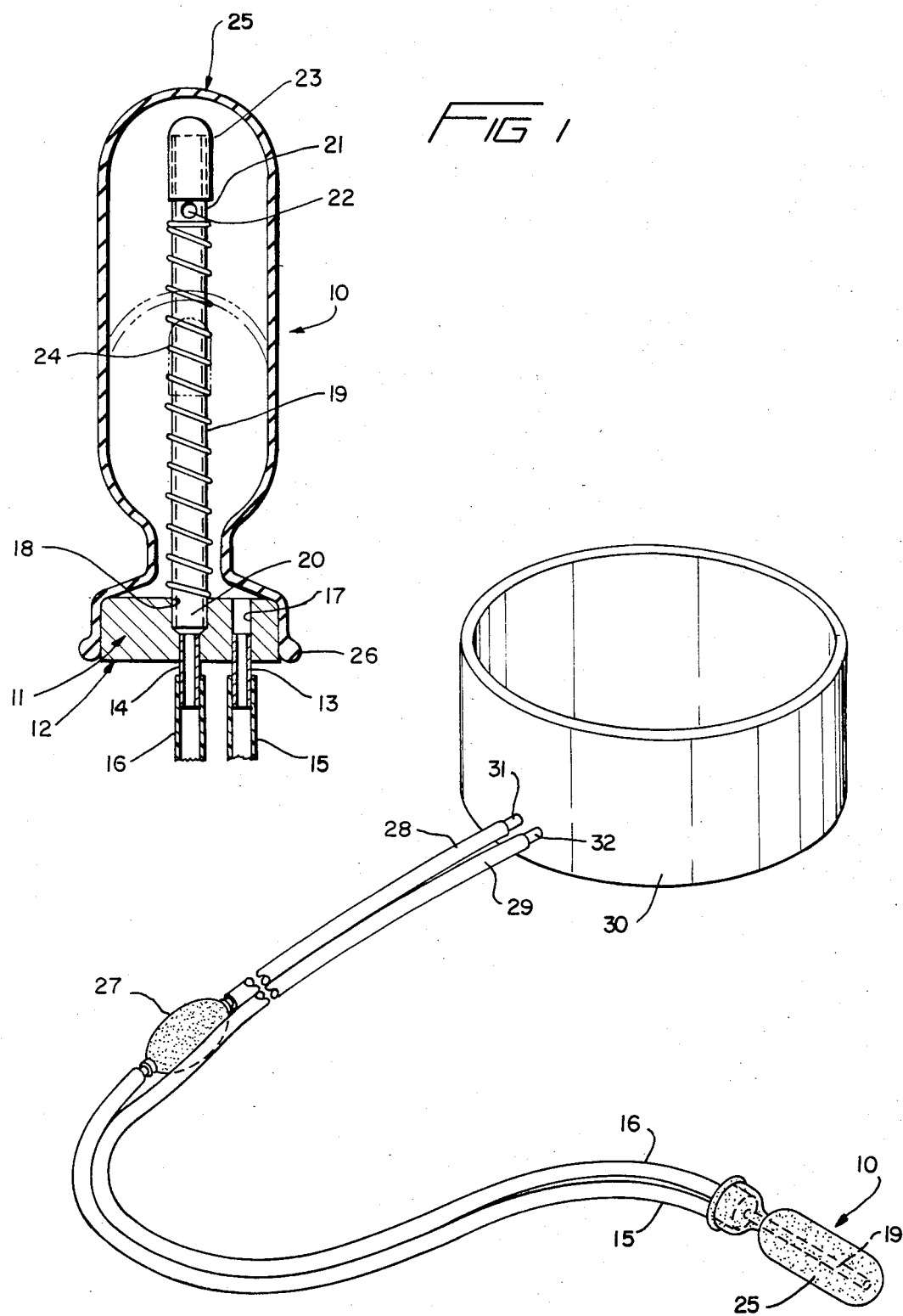

RECTAL HEMORRHOID THERAPEUTIC APPARATUS

BACKGROUND OF THE INVENTION

The invention relates to an apparatus for providing topical hemorrhoid therapy either via heat or cooling as desired by the user.

There are devices known which provide for topical therapy, not necessarily for hemorrhoids, such as the patent to Newman, U.S. Pat. No. 2,190,383, which provides a flexible applicator bag with inlet and outlet means, but which requires pressurization by a gas charge in the applicator bag and encompasses the use of electric pumping means and heating means for the therapeutic fluid. Because of the absence of internal support it is not clear that this device would be efficacious as a rectal inserter.

Another prior art device is that disclosed in the Zichlin U.S. Pat. No. 2,345,245 which encompasses a hard-shelled inserter device, constructed of "Lucite" or the like, with inlet and outlet means for supplying hydraulic fluid to heat or cool the device. An electrode heating means is provided centrally of the insertion device which renders this device quite complicated in construction and potentially less safe to use.

Still another prior art device is the topical hypothermia device disclosed in Wolvek et at, U.S. Pat. No. 4,111,209. This method for therapy provides a bladder for insertion into the heart for use in cardio-pulmonary surgery to lower the bood temperature to prevent hemorrhaging. While a bag-like device with fluid entrance and exit apertures is provided with a double lumen, the device is designed to be inserted wholly within an organ, such as a heart or uterus, and inflated to a sustainable position by fluid under pressure. The device is substantially different in construction and the method is different in use from that of applicant.

The final prior art device which is relevant to this apparatus is a product sold under the trademark ZEROID. The ZEROID device provides a sealed inserter in which coolable fluid is disposed. The inserter is refrigerated so as to freeze the fluid which releases its cooling effect to the hemorrhoidal region while thawing. The only way to continue the therapy is to refreeze the unit. No provision is made for warming therapy and there is no way to provide a specific cooling level above freezing for particularly sensitive persons whose rectal region could not stand such cold exposure.

OBJECTS OF THE INVENTION

It is an object of the invention to provide a simple, efficient apparatus for topical therapeutic application of warmth or cooling to body apertures.

It is another object of the invention to provide a therapeutic apparatus which is particularly suited to hemorrhoid therapy.

It is still another object of the invention to provide a therapeutic apparatus which is adapted for portable use.

It is yet another object of the invention to provide a therapeutic apparatus in which the therapy may be continued for prolonged periods by renewal of the cryogenic fluid resource through a pump and reservoir attachment.

It is yet a further object of the invention to provide a therapeutic apparatus in which the inserter head covers can be easily changed to provide therapy to orifices of the body requiring varying size and shape inserters, or to allow multiple persons in a family or health facility to use the same apparatus without a complete change of the whole inserter for reasons of health, safety and cleanliness.

SUMMARY OF THE INVENTION

The invention comprehends a novel, adjustable, flexible inserter head having a double lumen fluid feed via a hand pump from a reservoir means. The invention includes spring means to protect the outlet of fluid from collapse of the head cover by disposition over an internal outlet rod through which the cryogenic fluid exits to the reservoir. The stationary rod can be replaced so as to shorten the inserter and vary the original extended, slim head cover to a blunter, stouter configuration.

DESCRIPTION OF THE DRAWINGS

A more complete appreciation of the invention and many of the advantages attendant thereto will be developed by reference to the following detailed description, taken with reference to the accompanying drawings, in which:

FIG. 1 is an elevational view of a complete apparatus following this invention with a dashed line variant therefor; and FIG. 2 is a diagrammatic view illustrating a preferred embodiment of the whole invention as a unit.

DESCRIPTION OF THE PREFERRED EMBODIMENT

Referring now to FIG. 1, there is shown the complete inserter apparatus 10, comprising a generally circular base portion 11 provided with a bottom portion 12 from which offstand a pair of hose barbs or nipples 13, 14, nipple 14 being disposed centrally of the bottom portion 12, while nipple 13 is disposed radially outward from it proximate to the circumferential edge of the base. Each nipple 13, 14 is provided for association with a length of tubing, one for fluid inlet and one for fluid outlet to a reservoir 30 as shown in FIG. 2. The inlet nipple 13 is adapted to receive securely tubing end 15 and nipple 14 is adapted to receive securely tubing end 16. The nipples 13, 14 are axially aligned with apertures 17, 18, respectively, in the base to allow for fluid passage therethrough. Aperture 18, centrally disposed in the base, is provided with an end 20 of a tubular rod 19 securely disposed therein.

On an opposite extremity 21 of the tubular rod 19 is disposed a cap 23 covering and sealing the end of the tubular rod, while an aperture 22 is disposed adjacent the cap 23, through which the cryogenic fluid supplied via inlet nipple 13 may exit for return to the reservoir via tubular rod 19 and nipple 14. About the exterior wall of tubular rod 19 there is disposed a spring 24 which separates the tubular rod from a flexible cover 25, which might otherwise tend to collapse and cover the outlet aperture 22 in the tubular rod upon insertion of the inserter into a body cavity, such as the rectum. The cover is provided with a baseengaging gripping means 26 such as an elastic annular rib.

As can be seen in the dashed lines in FIG. 1, this device can be shortened by removal of the cover and replacement of the tubular rod. Thereupon, a variant shape, blunter and fatter in configuration, can be created and the device used in perhaps another differently sized body cavity, e.g., the mouth or the vagina. Advantageously, many shapes and sizes of inserter bulb can be achieved from the basic apparatus by varying the length of the tubular rod.

FIG. 2 shows the inserter apparatus coupled to a double lumen of tubing 15, 16 in which the tubing 15 is connected to the inlet nozzle 13 and in inlet branch a hand pump 27 can be disposed. Connectors 28, 29 are connected to an insulated reservoir 30 via further nipples 31, 32 respectively. In operation, the hand pump circulates cryogenic fluid from the reservoir 30 into the inserter bulb through tube 15 via nipple 13, to thereupon fill and circulate within the bulb cover 25, for return via the outlet 22 in tubular rod 19, and back to the reservoir via tubing 16.

As can be readily observed, many variants may be achieved for topical therapy by minor adjustment of the rod to re-define the inserter bulb cover size and shape, and to vary the caloric content of the fluid used as the therapy exchange medium, from hot to all but freezing, the sole limitation being the temperature constraints of the fluid medium for therapy.

Naturally, other modifications and variants to the present invention are possible in light of the above teachings. It is to be understood that such modifications are comprehended by the invention, the scope of which is not limited other than by the appended claims.

What is claimed and desired to be secured by letters patent of the United States is:

1. A topical hemorrhoid therapy apparatus, comprising in combination, an inserter having a base, a central aperture in said base, a second aperture in said base radially spaced from said central aperture in said base, a tubular rod means with one end disposed in said central aperture in said base, a cap secured over an extremity of said tubular rod means remote from said base, a third aperture in said tubular rod means which allows fluid to flow through said rod means, a flexible cover secured over said rod and secured to an outer circumference of said base by an elastic means for snug engagement with said base, first and second hose nipples extending from a bottom portion of said base and connected with said central aperture and said second aperture, respectively, said central aperture and said first nipple connected thereto serving as a unitary outlet means for fluid flowing from within said flexible cover, said second aperture and said second nipple serving as a unitary inlet means for fluid flow into said inserter, inlet and outlet tubing members connected to said nipples, and means surrounding said tubular rod means to prevent said cover from obstructing fluid entry into said third aperture whereby said inserter may provide topical therapeutic benefit to a bodily orifice such as the rectum.

2. A device as claimed in claim 1, further comprising a fluid reservoir means, each of said tubing members are connected to said reservoir means, a pumping means in said inlet tubing member between said inserter and said fluid reservoir means, said reservoir means being insulated to maintain temperature of a fluid contained therein, said fluid being selectively heatable and coolable.

3. A device as claimed in claim 1, wherein said means surrounding said rod means is a spring means.

* * * * *